United States Patent [19]
Beerstecher et al.

[11] Patent Number: 5,723,090
[45] Date of Patent: Mar. 3, 1998

[54] METHOD FOR THE HYGIENIC PREPARATION OF MEDICAL INSTRUMENTS

[75] Inventors: Lutz Beerstecher, Bensheim; Ralf Sutter, Weinheim; David Hruza, Bad Waldsee; Raimund Stetter-Alle, Ulm; Karl Trackl, Langenau, all of Germany

[73] Assignee: Siemens Aktiengesellschaft, Munich, Germany

[21] Appl. No.: 665,887

[22] Filed: Jun. 19, 1996

Related U.S. Application Data

[62] Division of Ser. No. 274,324, Jul. 13, 1994, Pat. No. 5,571,488.

[30] Foreign Application Priority Data

Jul. 15, 1993 [DE] Germany .............. 43 23 815.7
Apr. 26, 1994 [DE] Germany .............. 94 106 517.9

[51] Int. Cl.$^6$ ............... A61L 2/00; A61L 9/00
[52] U.S. Cl. ............... 422/26; 422/27; 422/28; 422/297; 422/300; 134/94.1; 134/100.1
[58] Field of Search ............... 422/26, 27, 28, 422/297, 388; 134/94.1, 100.1

[56] References Cited

U.S. PATENT DOCUMENTS

| | | | |
|---|---|---|---|
| 3,811,408 | 5/1974 | Thompson | 118/73 |
| 4,400,357 | 8/1983 | Hohmann | 422/297 |
| 4,541,992 | 9/1985 | Jerge et al. | 422/300 |
| 4,752,444 | 6/1988 | Bowen et al. | 422/28 |
| 5,057,283 | 10/1991 | Guggenheim et al. | 422/116 |
| 5,197,499 | 3/1993 | Bodenmiller et al. | 134/95.2 |
| 5,217,698 | 6/1993 | Siegel et al. | 422/295 |
| 5,225,160 | 7/1993 | Sanford et al. | 422/28 |
| 5,271,893 | 12/1993 | Newman | 422/26 |
| 5,275,668 | 1/1994 | Dell et al. | 134/10 |
| 5,290,511 | 3/1994 | Newman | 422/26 |
| 5,294,413 | 3/1994 | Riihimaki et al. | 422/297 |
| 5,348,711 | 9/1994 | Johnson et al. | 422/300 |
| 5,350,064 | 9/1994 | Schneck | 206/368 |
| 5,368,821 | 11/1994 | Schmoegner et al. | 422/116 |
| 5,520,892 | 5/1996 | Bowen | 422/295 |

FOREIGN PATENT DOCUMENTS

| | | |
|---|---|---|
| 0 429 960 | 6/1991 | European Pat. Off. |
| 30 18 872 | 11/1981 | Germany |
| 31 17 264 | 11/1982 | Germany |
| 39 16 446 | 3/1990 | Germany |
| 40 24 171 | 2/1992 | Germany |
| 41 30 233 | 9/1992 | Germany |
| 42 11 744 | 4/1993 | Germany |

*Primary Examiner*—Nina Bhat
*Attorney, Agent, or Firm*—Hill, Steadman & Simpson

[57] ABSTRACT

A method for cleaning medical instruments including dental instruments having internal channels and internal moving parts comprises cleaning the external surface and internal channels and parts by a jet of cold water followed by a jet of preheated water, then intensely after-cleaning and disinfecting followed by lubricating the moving parts, then sterilizing and drying and cooling.

15 Claims, 8 Drawing Sheets

METHOD FOR THE HYGIENIC PREPARATION OF MEDICAL INSTRUMENTS

This is a division of U.S. Ser. No. 08/274,324, filed Jul. 13, 1994, which issued as U.S. Pat. No. 5,571,488 on Nov. 5, 1996.

BACKGROUND OF THE INVENTION

The present invention is directed to a method and an apparatus for the hygienic preparation of medical instruments, particularly dental instruments, which may or may not have media channels and may or may not have moving internal parts.

U.S. Pat. No. 5,271,893, whose disclosure is incorporated herein by reference thereto and which is a continuation of an application which was the basis of European 0 429 960 and German Patents 41 30 233 and 42 11 744 each disclose an apparatus with which instruments can be sterilized. However, cleaning of the instruments as well as caring for the instruments by lubricating moving parts is not suggested or possible in these devices.

U.S. Pat. No. 5,197,499, whose disclosure is incorporated herein by reference thereto and which claims priority from German Application 40 24 171, discloses a method for caring, in particular for medical and dental instruments. In this care method, the instruments are subjected to the following method steps in an uninterrupted implementation of the method and at a single care location that allows all the method steps. These method steps are outside cleaning, disinfection, internal drying and care, after-cleaning as well as outside drying and cooling.

The instruments to be cared for are immersed for this purpose into a washing chamber where they are subjected to the above-mentioned method steps. The exterior cleaning occurs initially by blowing out the instruments with cold air, whereby the exterior rinsing with the water occurs and this is placed in motion by the air that is blown in. After this, hot water is admitted into the washing chamber, the instruments are then sterilized in the water bath. This method step is followed by an interior drying and care of instruments. To that end, they are blown out with hot air, then oil is blown into the instrument by the hot air. The after-cleaning following thereupon comprises the removal of excess oil in the inside of the instruments by blowing hot air in with elevated pressure. The instruments, moreover, are again treated with hot water which is introduced into the washing chamber. The drying occurs on the basis of the heat remaining in the instruments. For cooling, cold air is blown into the washing space. The duration of the entire procedure is approximately 20 minutes.

Apart from the fact that the relatively long heating time is required for heating the contents of the washing chamber, a comparatively greater quantity of water and, thus, much energy is required in this known method. In addition, the adding of surfactants or cleaning agents is required in order to achieve an acceptable cleaning effect. A further disadvantage may be seen wherein the instruments treated with this method must also be subsequently sterilized if they are to be sterile, for example in an autoclave of the species initially cited.

SUMMARY OF THE INVENTION

It is an object of the present invention to provide an improved method over those known to enable an optimum hygienic preparation of medical and dental instruments in a single apparatus.

To accomplish this, the method proposes that the instruments are placed into a chamber that can be closed pressure-tight and which the following steps can be automatically sequenced therein in a preselected process. The steps of the method comprise:

a) cleaning the exterior surfaces of the instrument as well as potentially any immediate channels with a high-energy water jet which is designationally directed onto the instruments, first with cold water and subsequently with a pre-heated water;

b) intensive after-cleaning and disinfection of the exterior surfaces and, potentially, of the media channels as well as of the moving internal parts and their bearings by blowing off and out with a water stream at a temperature between approximately 60° C. and 100° C.;

c) caring for the moving internal parts and their bearings of the instrument by injecting a metered quantity of lubricant; then d) sterilizing the instruments inside and out with saturated water steam at a temperature of, preferably, 130° C.; and then e) drying and cooling the instruments with a coolant, preferably with compressed air.

According to an advantageous development of the method of the invention, an intermediate drying of the gas, preferably with compressed air, occurs following the method step of intensively after-cleaning and prior to the caring step.

The caring step advantageously occurs with an oil/air mixture.

It is advantageous to evacuate the sterilization chamber before the sterilizing step in order to partially remove the dry air present within the cavities of the instrument. In addition, it is advantageous to promote the drying process with a vacuum.

In order to offer the user possibilities of taking instruments that need not necessarily be subjected to all the method steps from the apparatus as needed, the apparatus is provided with means in which the method can be interrupted at least following the care step. Likewise, it is advantageous to potentially skip or, respectively, omit one of the method steps, for example the method step of sterilizing.

A critical effect of the cleaning or, respectively, after-cleaning lies wherein the high-energy water jet is generated with a gas, preferably with compressed air that is supplied to the water surge-like. The pulse frequency for this surge-like delivery of gas lies in the range of 1 Hz to 10 Hz and preferably at 3 Hz. An especially good cleaning effect is achieved when the water is also supplied in a pulsating fashion, whereby the gas is supplied in the pulse pauses of the water delivery.

As tests have shown, extremely effective cleaning is achieved with the gas pulses supplied in alternation with the water in this manner. A further advantage is that the energy content of the cleaning agent, i.e., the water/air mixture, is preserved by the surge-like delivery of the gas with the available water pressure fluctuates or, respectively, is low. The cleaning effect becomes largely independent of the available water pressure.

Other advantages and features of the method as well as the apparatus for performing the method are readily apparent from the following description of the preferred embodiments, the claims and drawings.

3

Figure 2:
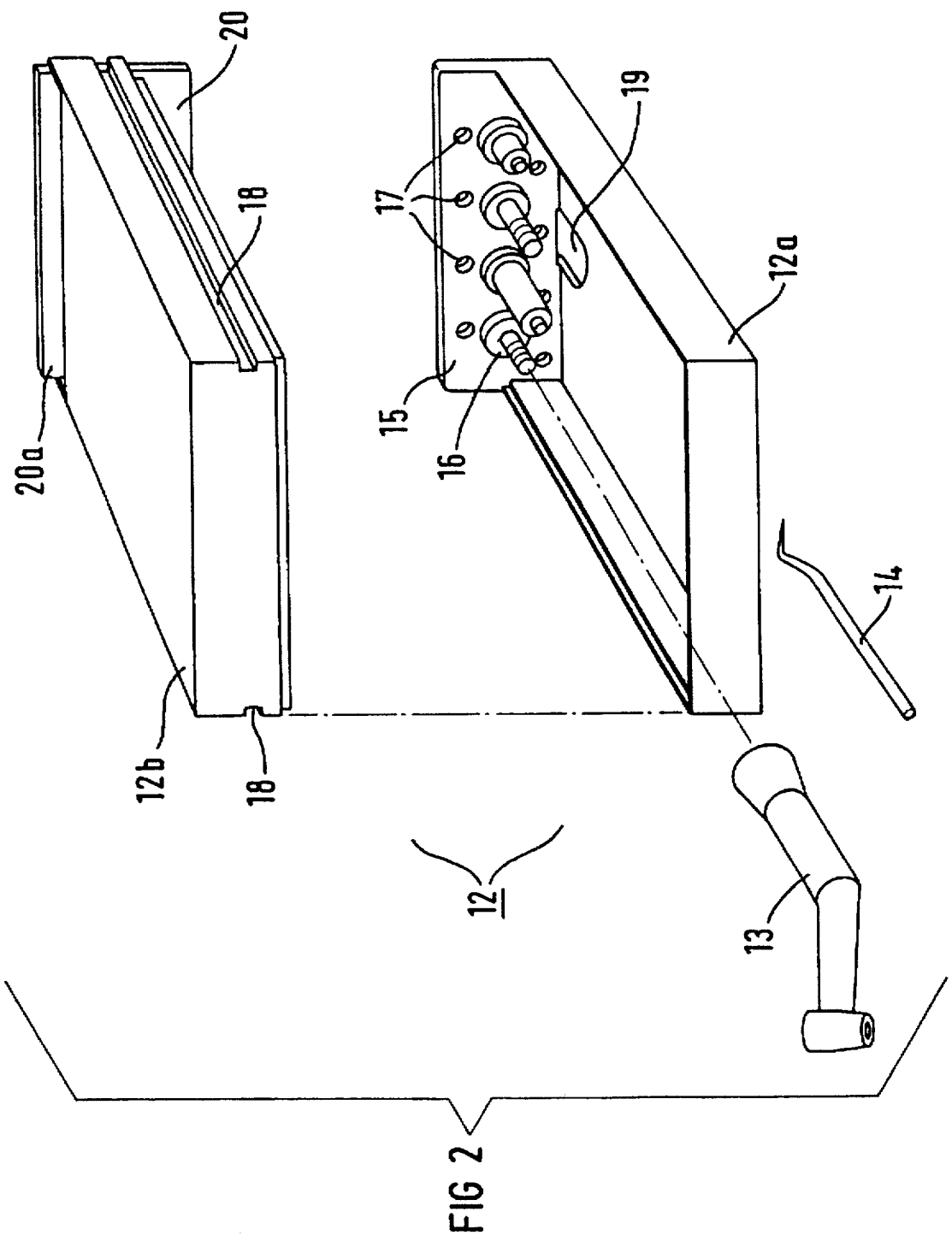
Figure 3:
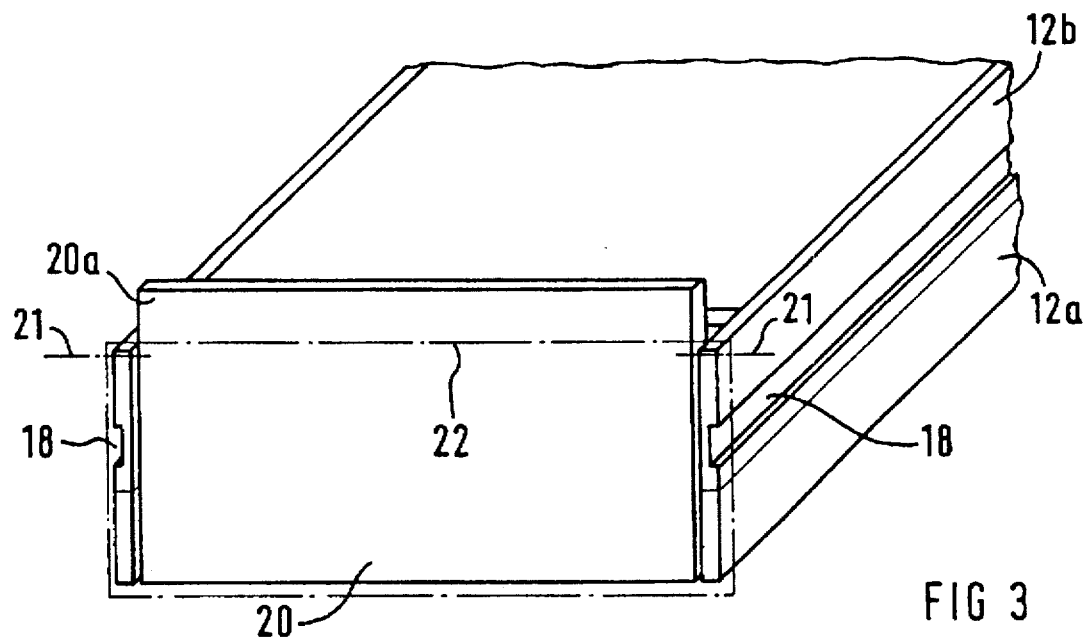
Figure 4:
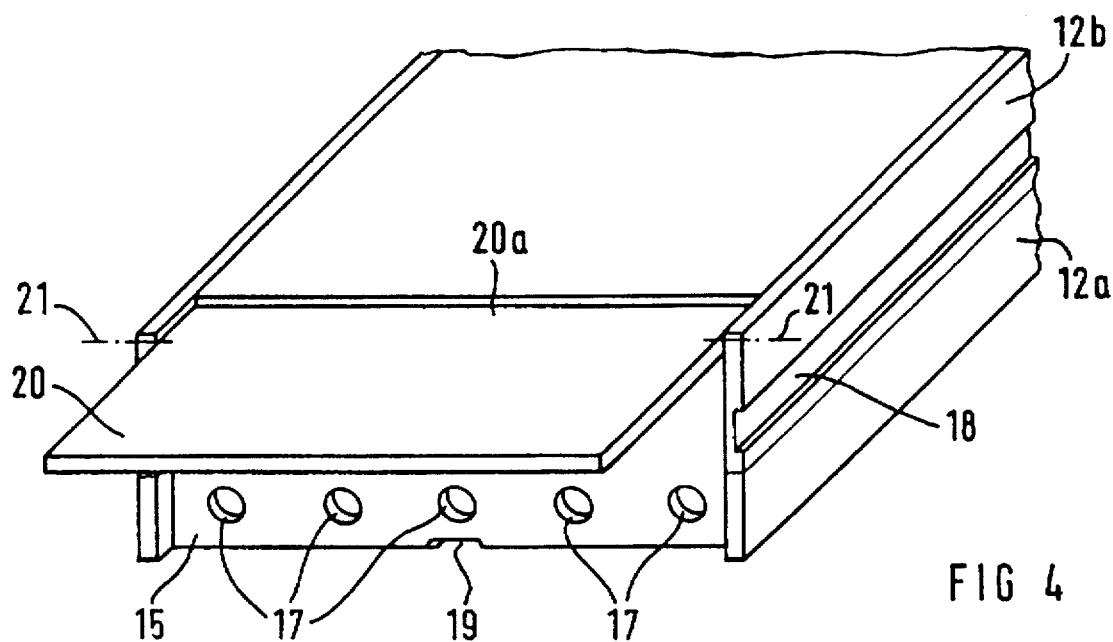
Figure 5:
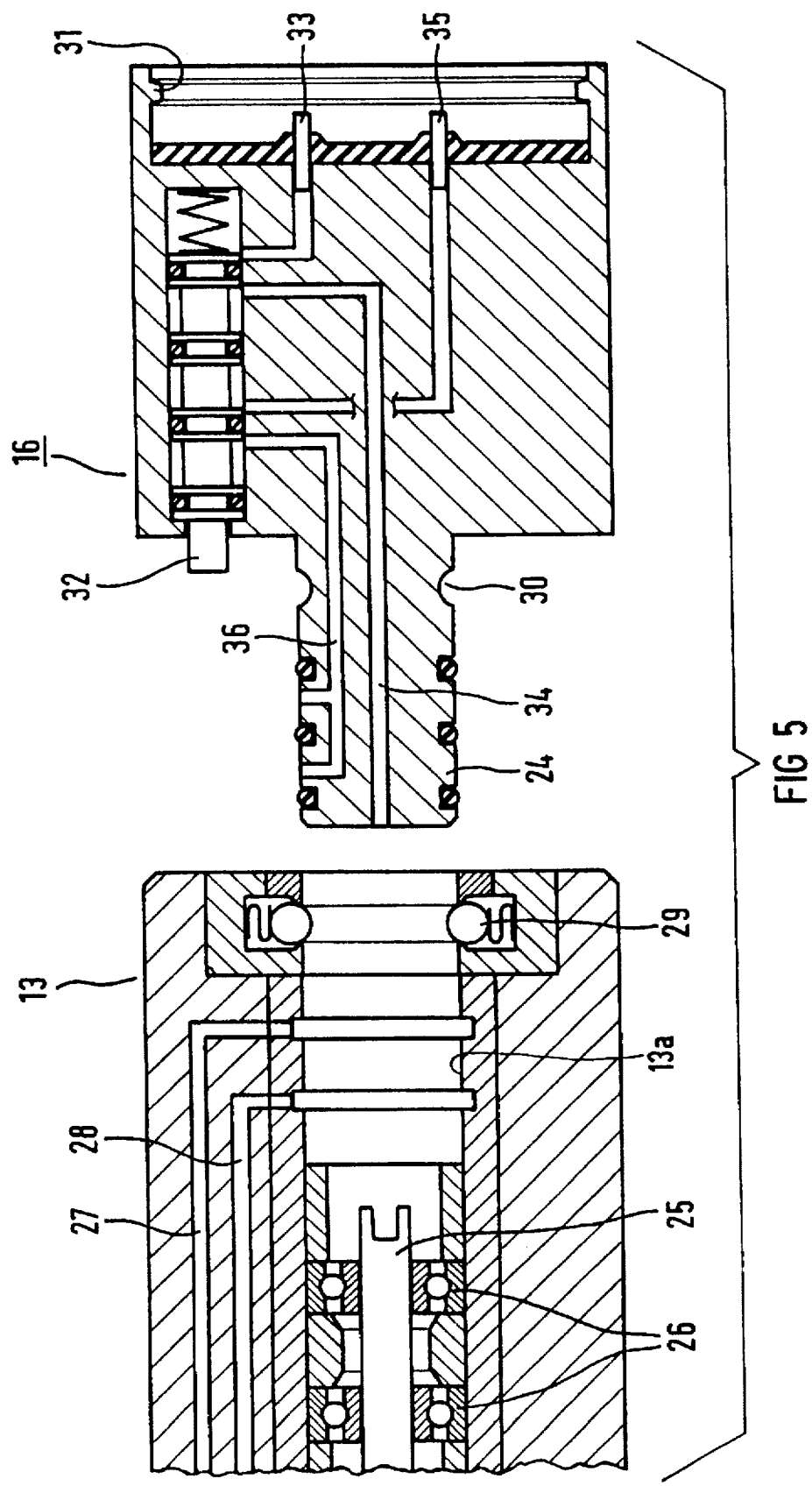
Figure 6:
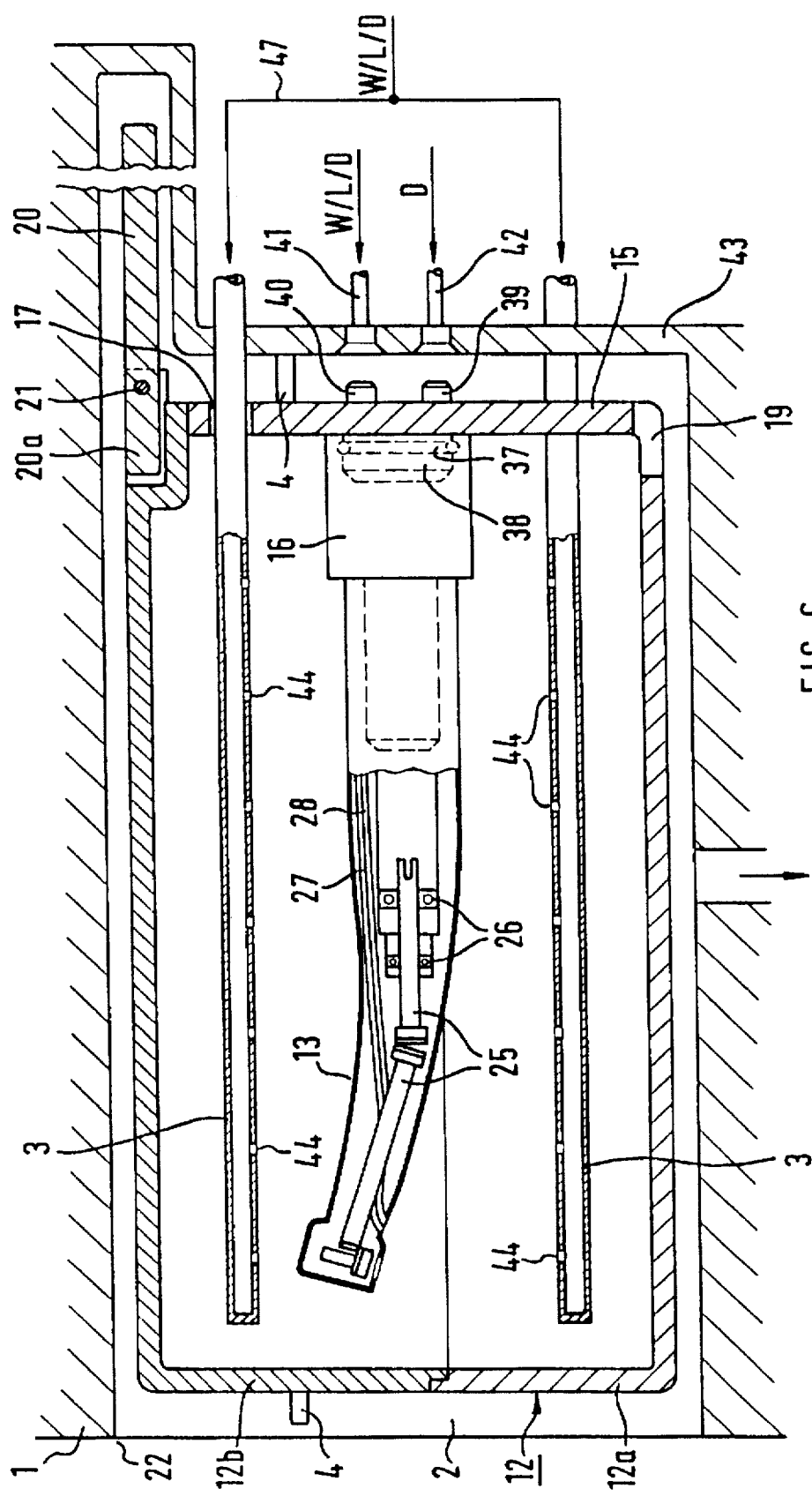
Figure 7:
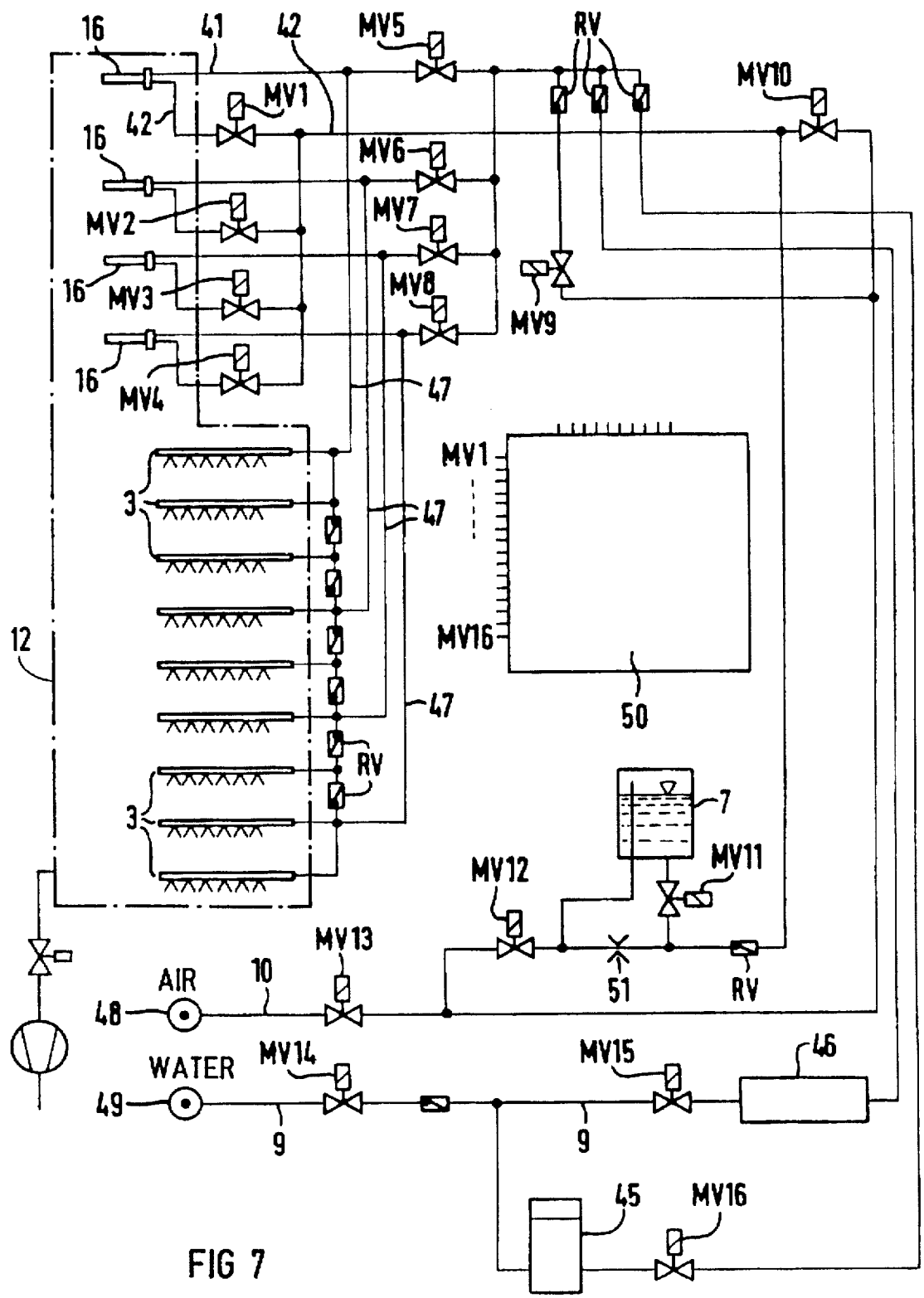
Figure 8:
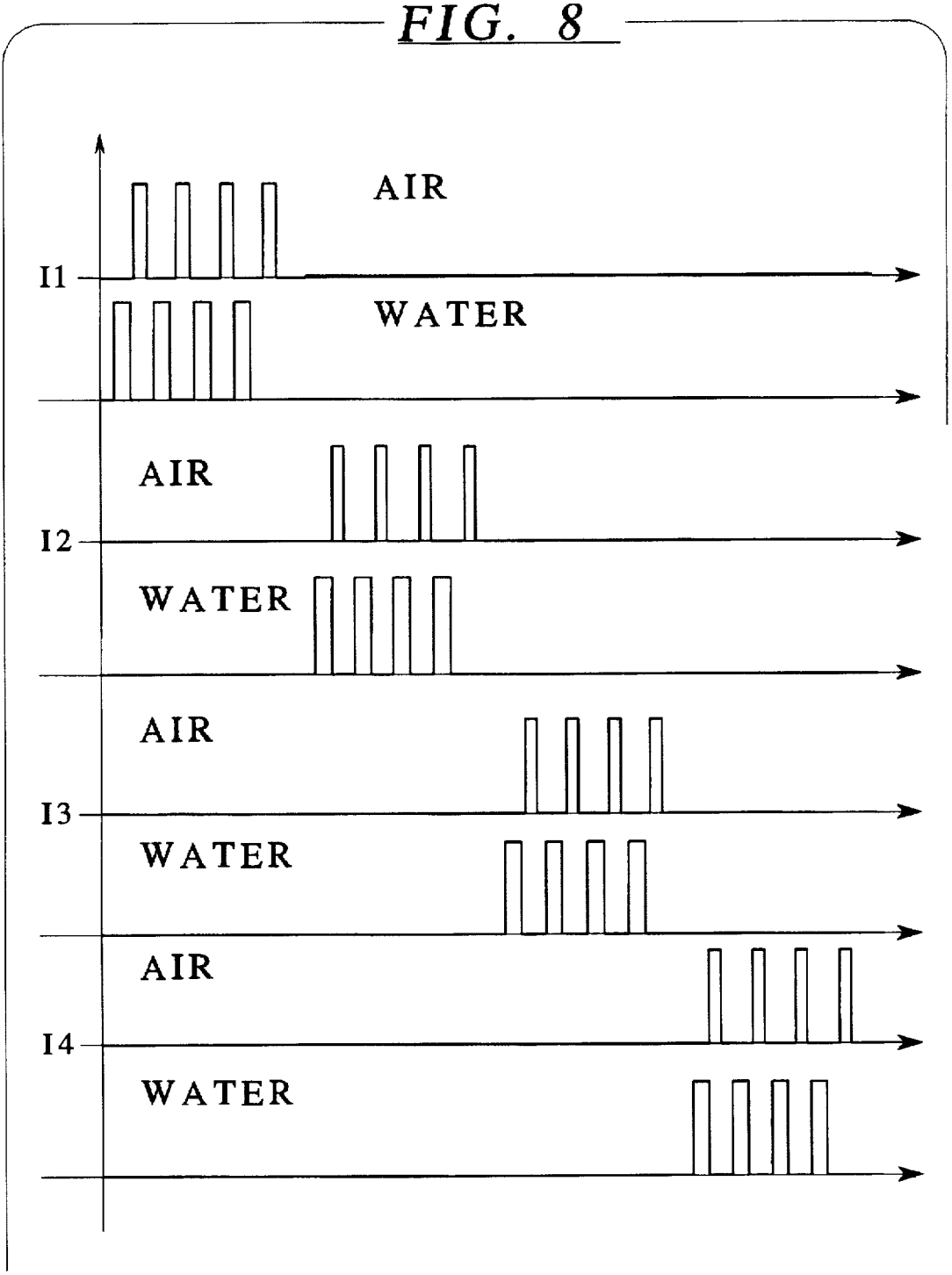
Figure 9:
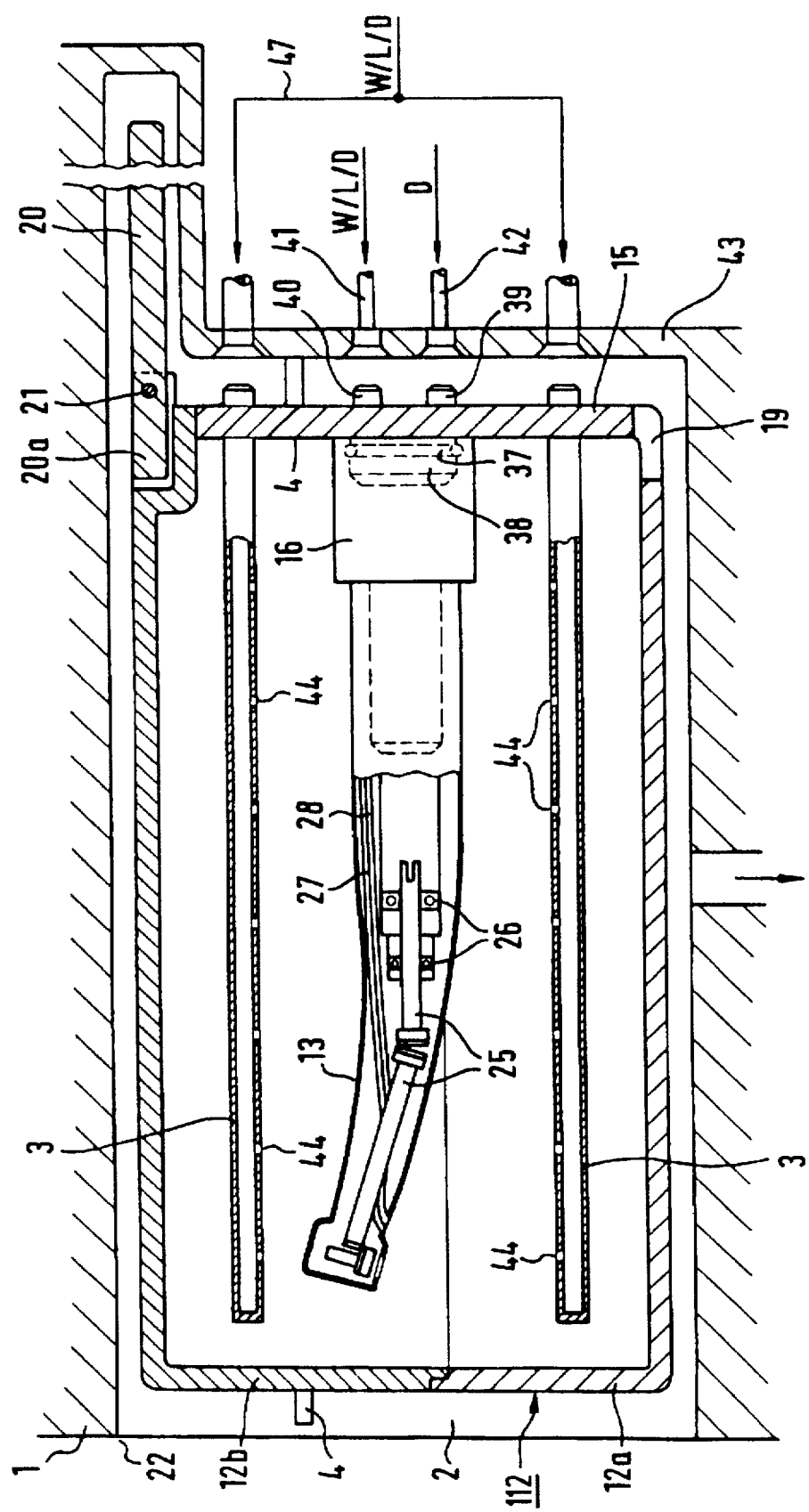

FIG. 2 is an exploded perspective view of an instrument cassette in accordance with the present invention;

FIG. 3 is a partial perspective view taken from the rear of the cassette with a closure flap in the closed position;

FIG. 4 is a partial perspective view similar to FIG. 3 with the closure flap in the opened position;

FIG. 5 is a longitudinal cross sectional view through an adapter illustrated in FIG. 2 and a portion of an instrument mating with the adapter;

FIG. 6 is a longitudinal cross sectional view of the cassette of the present invention disposed in the apparatus with portions in elevation for purposes of illustration;

FIG. 7 is a diagram illustrating the hydraulic and pneumatic connections of the present invention;

FIG. 8 is a diagram illustrating the sequence of pulses with respect to time during operation of the device of the present invention; and FIG. 9 is a modification of the apparatus and cassette illustrated in FIG. 6.

DESCRIPTION OF THE PREFERRED EMBODIMENTS

Figure 1:
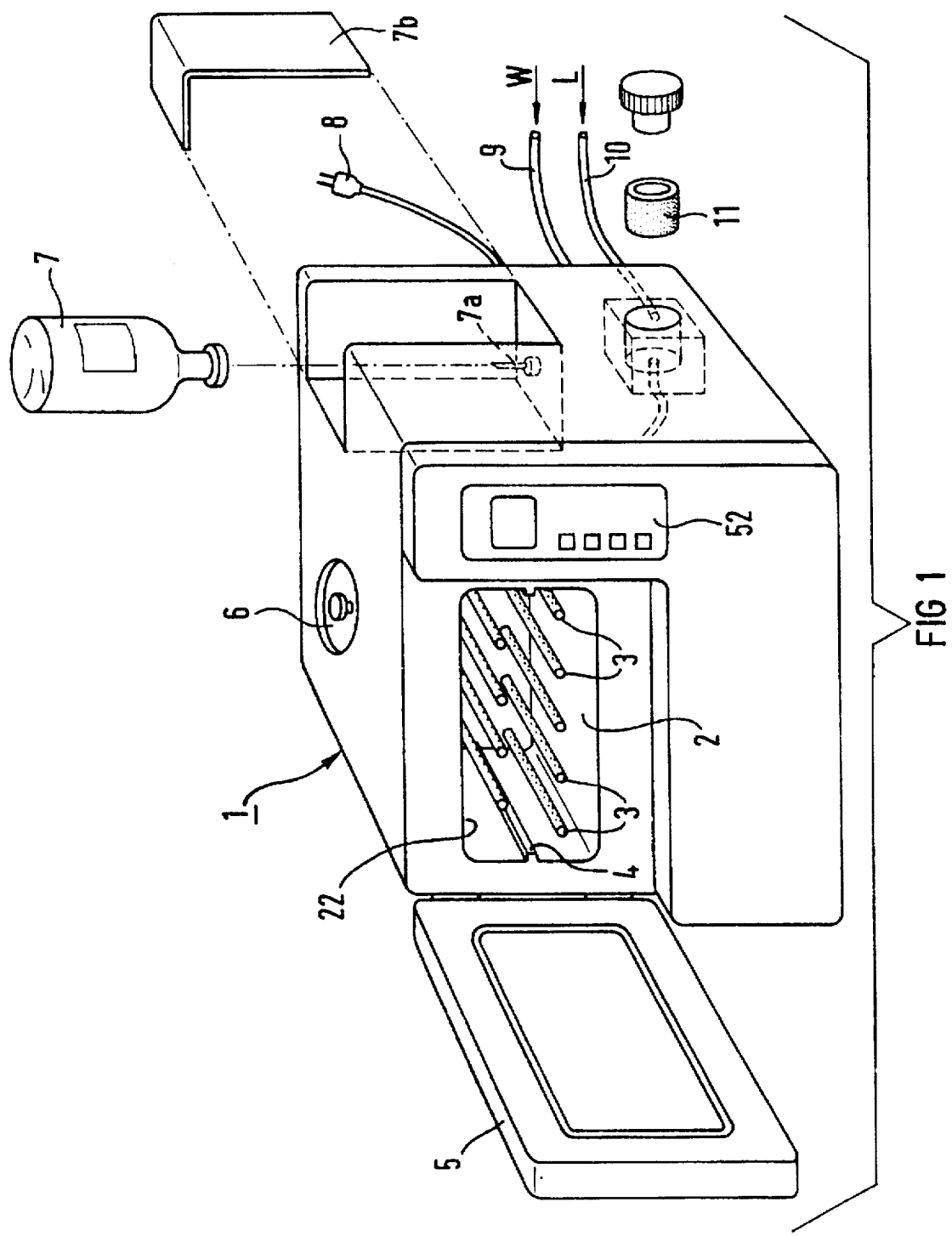
FIG. 1 is a schematic partially exploded perspective view of an embodiment of the apparatus of the present invention.

The principles of the present invention are particularly useful when incorporated in a cassette 12 illustrated in FIGS. 2 and 6, which is used with an apparatus, generally indicated at 1 in FIG. 1.

The apparatus 1 is used for the purpose of a hygienic preparation of various dental instruments. The apparatus contains a housing which forms a chamber 2 on the front side for the acceptance of a cassette 12 (see FIG. 2). The chamber 2 has a plurality of nozzle arms 3 (nine are illustrated) which project into the chamber 2. The instruments are capable of being sprayed on the outside with the assistance of these nozzle arms 3. The chamber 2 has guide beads 4 for the guidance of the cassette arranged on both sides. The chamber 2 can be closed pressure-tight on its front side with a cover or door 5, which operates in a known way.

The housing for the apparatus 1 has a container for demineralized or distilled water which is located adjacent an upper surface of the housing and has a filling opening 6. On the right-hand side near the rear of the apparatus, the apparatus 1 has a diaphragm closure provided in a known way, which closure is punctured by a connection shank 7a when the container 7 is placed on the connection shank so that removal of the lubricant can occur. A door or lid 7b can close the nitch that receives the container 7 once the container has been inserted.

The apparatus also has an electrical lead 8, a line 9 for receiving water indicated by the arrow W and an air line 10 which receives compressed air indicated by the arrow L. To assure that a largely germ-free gas or air is available for the method steps set forth in greater detail below, the air line 10 passes through a filter chamber which receives a removable and, thus, replaceable sterile filter 11.

The cassette 12, as illustrated in FIG. 2 in an exploded view, is introducible into the chamber 2 and will receive a plurality of instruments, such as a handpiece 13 and a manual instrument 14. The instrument 13 is shown as either a handpiece or an angle piece whose inside comprises various drive parts and bearings as well as media channels. The instrument 14, by contrast, is a hand instrument that comprises no moving parts and, therefore, has no media channels. The cassette 12 is composed of a base part or a lower part 12a and an upper cassette part 12b which is removable therefrom. The lower cassette part 12a is constructed trough-like and contains four different adapters for the acceptance of differently-shaped instruments on a raised backwall 15. In the exemplary embodiment, the adapter 16 is matched to receive the instrument 13 which is accepted thereon. The four adapters are provided for instruments that comprise moving internal parts and media channels, such as, for example, handpieces, angle pieces, turbine handpieces, handpieces for removing dental tartar or spring handpieces. The instruments that contain no moving internal parts and also contain no media channels, such as, for example, hand instruments 14 in the Figure, are placed on the floor or base of the lower cassette part with a suitable holder for the purpose of preparation.

The backwall 15 of the lower cassette part 12a also contains bores 17 (nine of which are illustrated), through which the nine nozzle arms or nozzle tubes 3 of the chamber 2 can pass through when the cassette 12 is introduced into the chamber. The arrangement of the nozzle arms and of the bores 17 which correspond thereto is, respectively, a triangular arrangement around the centrally-placed adapters, as illustrated in the Figure.

The upper part 12b can be placed on the lower cassette part 12a and can be latched thereto. The upper part 12b contains lateral guide channels 18 that interact with the above-mentioned guide beads 4 of the chamber and assure the exact centering and guidance of the cassette 12 when it is inserted into the chamber 2.

At a suitable location, preferably at the floor and in the immediate proximity of the backwall 15, the cassette is provided with one or more outlet openings 19 for the discharge of the supplied cleaning fluids, as well as any condensed water. This outlet opening or outlet openings are advantageously provided with a part that automatically closes when the cassette is removed from the chamber 2. These automatic closures can be spring-loaded slides or covers.

The upper cassette part 12b is advantageously provided with a cover on a back end, and this cover will cover, respectively, both the closing connections leading to the adapter 16 as well as the outlet openings 19 when the cassette is removed from the apparatus. As illustrated in FIGS. 3 and 4, the cover 20 is hinged around a bearing or axle 21. The movement of the cover occurs automatically when the cassette 12 is inserted into the chamber 2 of the apparatus. To accomplish this, the cover plate 20 comprises a projection 20a that strikes against the upper edge 22 (FIG. 1) of the chamber 2 upon insertion of the cassette 12 into the chamber. As a result of this, the flap will be tilted upward to the position illustrated in FIG. 4. Thus, the openings 17 located behind the cover plate, as well as the connections, which are not shown in FIG. 4, for the adapters will be uncovered or exposed. Upon removal of the cassette, the cover plate, in turn, automatically pivots or hinges down and, thus, covers the openings so that the hygienically prepared instruments located in the cassette are protected against the penetration of germs, at least for a certain time period.

Alternatively to the automatically opening and closing flap set forth above, a roller shutter element can also be provided. This will effect an automatic covering or, respectively, clearing of the openings or, respectively, connections provided in the backwall 15 with the assistance of a correspondingly provided setting means.

The structure and function of the adapters, as well as the interaction with the instruments that can be plugged thereon, is illustrated in FIG. 5 with reference to an example of the adapter 16.

The adapter 16 is provided for connecting a hand and angle piece 13 in FIG. 2. The hand or angle piece 13, as illustrated in FIG. 5, has an axial bore 13a which receives bearing 26 that mount a drive shaft 25 for rotation. In addition, the handpiece has media channels 27, 28 for delivering cooling air and cooling water to a preparation location, and these channels proceed on the interior of the handpiece. The bore 13a adjacent an open end is provided with ball catches 29, which will be received in an annular channel, similar to 30, of a motor housing when the handpiece is inserted thereon to form a connection therewith.

The adapter 16 contains a connecting shank 24 that is structurally matched to the design of the bore 13a of the instrument. The adapter 16 is fashioned so that the end facing away from the instrument can be secured to the backwall 15 of the lower cassette part 12a in an easily detachable way. To accomplish this, it contains a catch nose 31 that interacts with an annular channel 37 of a flange or nipple 38 (FIG. 6) that is mounted on the backwall 15 of the lower cassette part 12.

The adapter 16 has a bore containing a control plunger or spool valve member 32 that is displaceable parallel to the axis of the adapter, and this plunger 32 acts against a spring force so that when the instrument 13 is plugged onto the shank 24, the control plunger 32 is depressed so that the input channel 33 is connected to a centrally-placed channel 34 and an input channel 35 is connected to an aligned channel 36 which has peripheral openings that are aligned with openings for the media channels 27 and 28 of the instrument. Thus, drive air or lubricating oil can be introduced via the channel 33 to the drive shaft 25 and the bearings 26 and air and water are guided in common in the lines 27 and 28 via the channels 35 and 36.

When an instrument, such as 13, is removed from the adapter 16, the plunger valve will assume the position illustrated in FIG. 5 and interrupt the connection between the inlet channel 33 and channel 34 and also between the channel 35 and channel 36. This will prevent any supplied media or oil from being emitted from an adapter which is not occupied with an instrument.

As already mentioned, the connection dimensions with respect to the instruments are different for all four adapters mounted in the cassette in order to, thus, be able to hold different instruments. The connecting dimensions with respect to the connector 38 on the backwall 15 of the cassette, however, are the same for all adapters so that they can be easily interchanged with one another or, respectively, can be replaced by adapters having different connecting contours for different instruments.

The allocation of the individual washing and cleaning nozzles or channels is illustrated in FIG. 6 with reference to an example of the instrument 13 and adapter 16.

In a highly simplified illustration, FIG. 6 shows the arrangement of the cassette 12 in the chamber 2 in the condition wherein the cassette 12 is nearly completely introduced. Corresponding to the plurality of existing adapters, connecting flanges 38 are located on a backwall 15 of the cassette 12 and the adapter is, as already mentioned, capable of being put in place on these connecting flanges 38 in an easily detachable way. The connecting flange 38 has a coupling sleeve 40 that will form a connection with a lead 41 and a sleeve 39 forms a connection with a lead 42. The lead 42 corresponds to the lead 35 for pressurized water, compressed gas or air and steam indicated by arrow W/L/D, while the lead 42 corresponds to the channel 33 for lubricant and air indicated by arrow D. Each of the nozzle arms 3 are arranged star-like or, respectively, triangularly around the instrument 13 and are firmly arranged in the housing wall 43 that defines the back side of the chamber 2. These tubes or arms 3 are connected to the line 47 to receive pressurized water, compressed gas and steam, as indicated by arrow W/L/D. The tubes or arms 3 are fashioned as hollow tubes and comprise a plurality of exit openings 44 that are arranged aligned at a specific angle to a surface of the instrument. The nozzle bores are advantageously arranged along the nozzle arm or tube not only in one plane but in a plurality of planes offset relative to one another by a defined angle. The offset can be advantageously arranged zig-zag or wave-like in the longitudinal direction along the reference plane.

As illustrated in FIG. 1, as well as from the following hydraulic and pneumatic connection diagram set forth in greater detail in FIG. 7, nine nozzle arms are advantageously provided for preparing a maximum of four instruments. The arrangement is therefore undertaken so that the nozzle arms are arranged in two rows and offset so that three arms are arranged around an instrument at a respective angle of 120° relative to one another.

Before the method of the invention is set forth in greater detail with reference to the drawings already described and with reference to the hydraulic and pneumatic block circuit diagram of FIG. 7, it should be pointed out that the steam generator 45 connected to the pressurized line 9, as well as the preheating means 46 for water, are accommodated in the apparatus housing in addition to the above-mentioned oil reservoir or container 7. Thus, it should be pointed out that the nozzle arms 3 length from the backwall is limited so that the lid 20 is able to tip from the closed position to the opened position as the projection 20a engages the edge 22 without striking the ends of the tubes 3.

In the hydraulic/pneumatic connection block diagram of FIG. 7, a compressed air supply source 48 and a pressurized water source 49 are connected through the lines 10 and 9, respectively. For purposes of illustration, the filters, oil separators for the compressed air as well as the overpressure valves that are standard on the input side are not illustrated for the sake of simplicity.

All solenoid valves MV1 through MV16, as well as the water heater 16 and the steam generator 45, are controlled by a microprocessor 50. Reflex or check valves RV are connected in all of the lines.

The injection of a lubricant (maintenance oil mixed with air) from the reservoir 7 occurs pneumatically here via two solenoid valves MV1 and MV12 as well as by a restriction point or throttle point 51. Alternatively, the lubricating oil could also be supplied with a suitable oil pump. The microprocessor 50 controls the valves MV1 through MV9 and MV11 through MV16 so that the agents of water, air and also lubricating oil can be supplied to the adapter 16 and to the nozzle arms 3 separately for each instrument during a method step of pre-cleaning, after-cleaning and, potentially, during the care procedure so that the instruments are cleaned and potentially maintained in chronological succession.

The chronological offset may be seen from the pulse/time diagram of FIG. 8 that shows the chronological course of the valve connections for the various agents of air and water for the four instruments referenced 11–14. A high cleaning efficiency given a low water consumption is achieved with this chronologically successive cut-in of the agents.

The method utilizing the cassette is as follows:

The cassette 12 is charged with instruments and the instruments that have movable internal parts, such as the angle pieces, turbines, sprays or the like, are plugged onto corresponding adapters 16 of which a maximum of four are allowed in the cassette. The other instruments are placed at a holder device above the floor of the container. The cassettes are then closed by putting the upper cassette part 12b on the lower part 12a and the cassette is introduced into the chamber 2 of the apparatus. During this insertion, the rear cover 20 is lifted and, as a result thereof, the nine nozzle arms 3 extend through the bores 17 of the backwall 15 of the cassette. After the cassette has been inserted into the chamber to such an extent that the connection of lines 41 and 42 with the connectors 39 and 40 (see FIG. 6) has been produced, the cover 5 of the apparatus is closed and the apparatus is turned on.

After a self-test, which lasts approximately half a minute, a cold cleaning of the instruments occurs utilizing cold water which is supplied to the adapter 16 and to the nozzle arms 3 via leads 9 and the lines 41 and 47. The cold water is preferably supplied in a pulsating fashion whereby compressed air at high pressure, which is also pulsating, is mixed with the water into the pulse pauses illustrated in FIG. 8. A high-energy water jet is thus produced and this surprisingly causes a very thorough cleaning of the surfaces and of the inside channels as well. At the same time, the gearing channel is charged with air via a line 42 with the oil delivery valve MV11 remaining closed so that the penetration of dirt and contaminated wash water is therefore prevented. The pulse frequency with which the compressed air is supplied to the water amounts to approximately 3 Hz.

The cold cleaning is ended after about two minutes. The warm cleaning of the exterior surfaces of the instrument and of the inside channels follows thereafter, likewise with a pulsating water jet upon addition of pulsed compressed air. This procedure follows the sequence in the above-mentioned way. After about two minutes of warm cleaning, an intense after-cleaning and a vapor disinfection occurs by blowing the exterior surface of the instruments and of the media and gearing channels in the interior of the instrument off and out with the hot water or water vapor at a temperature in a range of 60° C. through 100° C. To this end, the water is heated by the heater 46 which acts as a flow-through heater. This procedure lasts for about 30–45 seconds.

Care of the moving inside parts follows this intensive after-cleaning by injecting a metered quantity of lubricant from the lubricant reservoir 7. The metering can occur dependent on the adapted instrument and amounts to about 1 gram per instrument in the injection cycle on average. This maintenance step lasts approximately half a minute.

A sterilization of the instrument then subsequently occurs, namely both from the outside as well as from the inside with saturated water steam at a temperature of approximately 134° C. given a pressure of approximately 2–2.5 bar. The sterilization procedure amounts to between 5 and 6 minutes. The sterilization procedure is followed by a drying and cooling of the instrument with cold air. The cooling procedure lasts approximately 3–5 minutes. Given an overall time of approximately 15–20 minutes for preparing the instruments, the cassette 12 with the prepared instruments can be subsequently removed and can be kept ready for use in its closed condition.

The method of execution which automatically sequences in and of itself in the described way can be varied by intervention. For example, on the basis of an appropriate program, pre-selection can be called in at a control and display panel 52 (FIG. 1) on the front side of the apparatus 1, for example, in that an intermediate drying, for example with air, is implemented following the intensive after-cleaning and disinfection of the external surfaces. An interruption can likewise occur after the maintenance in order to be able to remove articles which are not to be sterilized from the cassette.

For removing existing dry air, particularly from cavities, and particularly from cavities of the instruments, the chamber can be evacuated before the sterilization of the instruments in an advantageous modification. In order to achieve an optimum removal of the dry air, the vacuum should lie in the range of between 40 mbar and 500 mbar absolute. The vacuum can be produced according to a known fractional, multi-step method or according to a pre-vacuum method.

Extremely short times for an optimum, hygienic preparation of the instrument occur with the described method. Due to the pulsating water jet to which high-energy compressed air is supplied in surges, an especially intense cleaning of the parts is obtained. A reliable transport to the treatment location is established in that the instruments can remain in the cassette after the preparation. In addition, the cassette may be used to receive used instruments and store these used or contaminated instruments until they are to be sent for preparation. The instruments contaminated with germs after being used remain in the cassette until they are taken again therefrom and, therefore, a risk of injury to the operating personnel, among other things, is precluded as a result of this procedure. Processing, storing and transport will occur in the cassette. Since the cassette is largely closed, a sterile storing of the instrument is assured over at least an adequately long time, as measured in hours. In that the internal parts and the agent channels are flooded with hot water and steam, a relatively rapid heating time for the overall instrument occurs. A certain lime-dissolving effect is also achieved in the lines due to the fact that the lines are blown out with the water and/or steam and the exteriors are blown off with the water and/or steam. A critical advantage is that no cleaning and drive agent whatsoever need be employed.

A modification or embodiment of the cassette is illustrated in FIG. 9 by a cassette generally indicated as 112. This modification is with regard to the nozzle arms 3. For example, the nozzle arms can be component parts of the cassette, as shown in the exemplary embodiment of FIG. 9, and are mounted in the backwall 15. In addition, even though this would be relatively involved, the nozzle arms can be pivoted around their longitudinal axis and can also be potentially arranged movable in an axial direction. The cover shown in FIGS. 3–5 can alternatively also be a component part of the lower cassette or can be allocated to both cassette halves.

Although various minor modifications may be suggested by those versed in the art, it should be understood that we wish to embody within the scope of the patent granted hereon all such modifications as reasonably and properly come within the scope of our contribution to the art.

We claim:

1. A method for hygienical preparation of medical instruments including dental instruments having media channels, dental instruments without media channels and dental instruments with movable internal parts, said method comprising the step of loading the instruments into a chamber, which is then closed pressure-tight; while in the chamber, performing the steps of cleaning exterior surfaces of each of the instruments as well as any existing media channels by directing a high-energy water jet onto the exterior surfaces of the instruments and into the existing channels, said high-energy jet being, first, a cold water jet and then subsequently using a jet with a preheated water; intensely after-cleaning and disinfecting the exterior surfaces and any existing media channels as well as any movable internal parts and bearings of an instrument by directing a water stream having a temperature range of 60° C. to 100° C. onto the exterior surfaces, through any existing media channel and through the movable internal parts and bearings; lubricating existing movable parts by injecting a metered quantity of lubricant; sterilizing the instrument on the exterior surfaces and in any media channels and movable parts with saturated steam of a temperature of approximately 134° C.; then drying and cooling the instrument with a coolant.

2. A method according to claim 1, which includes subsequent to the step of intensive after-cleaning and disinfecting and prior to the step of lubricating, conducting an intermediate drying with a coolant.

3. A method according to claim 1, wherein the step of injecting a lubricant occurs with an oil/air mixture.

4. A method according to claim 3, wherein the quantity to oil is automatically selected dependent on the instrument being involved.

5. A method according to claim 3, wherein the quantity of oil lies in a range of between 0.1 and 2 grams per instrument per injection cycle.

6. A method according to claim 1, wherein the step of drying and cooling occurs with compressed air.

7. A method according to claim 1, wherein the treatment space is evacuated before the step of sterilizing.

8. A method according to claim 1, wherein the step of drying is supported by creating a vacuum in the chamber.

9. A method according to claim 1, wherein the method lasts in a range of 10–20 minutes, wherein the individual step of cleaning takes approximately 3 minutes, the steps of intensively after-cleaning and disinfecting takes approximately 2 minutes, the step of lubricating takes approximately one-half of a minute, the step of sterilizing the instrument takes approximately 6.5 minutes and the step of drying and cooling takes approximately 3 minutes.

10. A method according to claim 1, wherein the step of cleaning includes providing a high-energy water jet by providing water under pressure with a gas supplied surge-like to said water.

11. A method according to claim 10, wherein a pulse frequency of the surge-like delivery of gas amounts to in a range between 1 Hz and 10 Hz.

12. A method according to claim 11, wherein the pulse frequency is 3 Hz.

13. A method according to claim 1, wherein the step of loading instruments loads more than one instrument and the steps of cleaning, intensive after-cleaning and disinfecting, and lubricating occur in a chronological succession for each instrument separately having media channels and movable internal parts.

14. A method according to claim 1, which includes interrupting the sequence of steps after the step of lubricating.

15. A method for hygienic preparation of medical, including dental, instruments with or without media channels and with or without movable internal parts, said method comprising the steps of inserting the instruments with at least one instrument having internal channels and movable interior parts into a closed pressure-tight chamber, and, while in the chamber, performing a sequence of preselectible processes including cleaning the exterior surfaces of all instruments as well as media channels of the instruments having media channels by directing a cold water jet onto the exterior surfaces of the instruments and through those media channels, subsequently directing a high-energy jet of preheated water onto the exterior surfaces and through those channels; intensive after-cleaning and disinfecting of the exterior surfaces and the immediate channels as well as movable internal parts and their bearings by blowing water at a temperature range of 60° C. to 100° C. on the exterior surfaces, through said channels and through said moving parts and bearings; lubricating for the movable internal parts by injecting a metered quantity of lubricant therein, and then drying and cooling the instrument with a coolant.

\* \* \* \* \*